United States Patent [19]

Miura et al.

[11] Patent Number: 5,019,574

[45] Date of Patent: May 28, 1991

[54] 3,4-DIAMINOQUINOLINE AND 3,4-DIAMINO-5,6,7,8-TETRAHYDROQUINOLINE COMPOUNDS USEFUL FOR IMPROVING PSYCHONEURAL FUNCTION

[75] Inventors: Yutaka Miura; Mitsutaka Yoshida, both of Shizuoka; Yasuo Fujimura; Sakae Takaku, both of Saitama; Yukifumi Noda, Shizuoka, all of Japan

[73] Assignee: Chugai Seiyaku Kabushiki Kaisha, Tokyo, Japan

[21] Appl. No.: 414,170

[22] Filed: Sep. 28, 1989

[30] Foreign Application Priority Data

Sep. 30, 1988 [JP] Japan ................................ 63-246237

[51] Int. Cl.[5] .................... A61K 31/525; A61K 31/47; C07D 413/00; C07D 215/42

[52] U.S. Cl. ................................ 514/235.2; 514/254; 514/312; 514/313; 544/128; 544/363; 546/157; 546/159; 546/160

[58] Field of Search ................ 544/128, 363; 546/157, 546/159, 160; 514/312, 313, 235.2, 254

[56] References Cited

FOREIGN PATENT DOCUMENTS 0145340 6/1985 European Pat. Off. .
0223420 5/1987 European Pat. Off. .
0329073 8/1989 European Pat. Off. .

OTHER PUBLICATIONS

Nay, B. et al. *Tetrahedron Lett.*, (21), 1811-12 (1977).
Hollywood, F. et al. *J. Chem. Soc. Perkin Trans. I*, (2), 421-9 (1982).
Sharma, K. S. et al., *Synthesis*, (7), 581 (1983).
Shindo, H. et al. *Heterocycles*, 29(5), 899-912 (1989).

*Primary Examiner*—Mary C. Lee
*Assistant Examiner*—Michael G. Ambrose
*Attorney, Agent, or Firm*—Browdy and Neimark

[57] ABSTRACT

4-aminopyridine derivatives represented by the general formula:

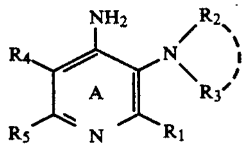

[wherein $R_1$ is a hydrogen atom, a hydroxyl group, a linear or branched lower alkyl group or a cycloalkyl group which may be substituted by a hydroxyl group, a lower alkoxy group, a lower alkyl or a cycloalkyl group which contains a carbonyl group, a morpholino group or a group —NH—B (where B is a lower alkyl group, a cycloalkyl group or a phenyl group); $R_2$ and $R_3$ which may be the same or different each represents a hydrogen atom, a lower alkyl group or a loweralkylcarbonyl group, or when taken together, form an azacycloalkyl group, a morpholino group or an N-methylpiperazinyl group together with the nitrogen atom; $R_4$ and $R_5$ each represents a hydrogen atom, or when taken together with the ring A, form a quinoline ring or a 5,6,7,8-tetrahydroquinoline ring, provided that when each of $R_1$, $R_4$ and $R_5$ is a hydrogen atom, $R_2$ and $R_3$ are neither a hydrogen atom nor a methyl group at the same time, and when $R_1$ is a hydrogen atom and $R_4$ and $R_5$ taken together with the ring A form a quinoline ring, $R_2$ and $R_3$ are neither a hydrogen atom nor an ethyl group at the same time], and an acid addition salts of said 4-aminopyridine derivatives. These compounds are useful as active ingredients in pharmaceutical compositions for improving psychoneural function, especially in the treatment of Alzheimer type dementia and promotion of mnemonic and learning performance.

11 Claims, 1 Drawing Sheet

3,4-DIAMINOQUINOLINE AND 3,4-DIAMINO-5,6,7,8-TETRAHYDROQUINOLINE COMPOUNDS USEFUL FOR IMPROVING PSYCHONEURAL FUNCTION

FIELD OF THE INVENTION

The present invention relates to 4-aminopyridine derivatives represented by the general formula (I):

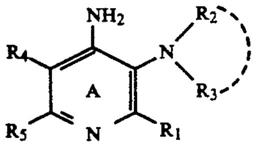

(I)

where $R_1$ is a hydrogen atom, a hydroxyl group, a linear or branched lower alkyl group or a cycloalkyl group which may be substituted by a hydroxyl group, a lower alkoxy group, a lower alkyl or a cycloalkyl group which contains a carbonyl group, a morpholino group or a group —NH—B (where B is a lower alkyl group, a cycloalkyl group or a phenyl group); $R_2$ and $R_3$ which may be the same or different each represents a hydrogen atom, a lower alkyl group or a loweralkylcarbonyl group, or when taken together, form an azacycloalkyl group, a morpholino group or an N-methylpiperazinyl group together with the nitrogen atom; $R_4$ and $R_5$ each represents a hydrogen atom, or when taken together with the ring A, form a quinoline ring or a 5,6,7,8-tetrahydroquinoline ring, provided that when each of $R_1$, $R_4$ and $R_5$ is a hydrogen atom. $R_2$ and $R_3$ are neither a hydrogen atom nor a methyl group at the same time, and when $R_1$ is a hydrogen atom and $R_4$ and $R_5$ taken together with the ring A form a quinoline ring. $R_2$ and $R_3$ are neither a hydrogen atom nor an ethyl group at the same time. The present invention also relates to an acid addition salts of said 4-aminopyridine derivatives.

BACKGROUND OF THE INVENTION

With the progress of "aging society", the population of aged persons has recently increased and the increase in the number of senile diseases is correspondingly rapid. Among various senile diseases, dementia is of particular importance since the mechanism of its occurrence has not been fully unravelled and it can be fatal depending on its severity. Under these circumstances, the advent of an effective therapeutic agent for senile dementia is strongly desired.

Numerous studies on senile dementia have been conducted to date. The phenomena that have been reported to occur in patients with senile dementia include impairment of the central cholinergic nervous function on account of decreases in the number of choline acetyltransferase (CAT) and acetylcholinesterase (AChE) which are enzymes that synthesize and decompose, respectively. acetylcholine known to be the transmitter of cholinergic neurons (see British Medical Journal, 2: 1457–1459, 1978; Brain, 107: 507–518, 1984; Journal of the Neurological Sciences, 57: 407–417, 1982; and Lancet, 2: 1403, 1976) and impairment of the central noradrenergic nervous function (see British Medical Journal, 282: 93–94, 1981). Researchers are making active efforts to develop drugs that are suitable for the symptomatic treatment of these phenomena.

SUMMARY OF THE INVENTION

Under the circumstances described above, the present inventors undertook intensive studies in order to develop a therapeutic agent effective in reactivating the nervous function impaired by senile dementia. As a result, they found that compounds represented by the general formula (I) exhibited unique pharmacological effects in that they activated the nervous function of animals and accelerated their mnemonic and learning performance. The present invention has been accomplished on the basis of this finding.

DETAILED DESCRIPTION OF THE INVENTION

Figure 1:
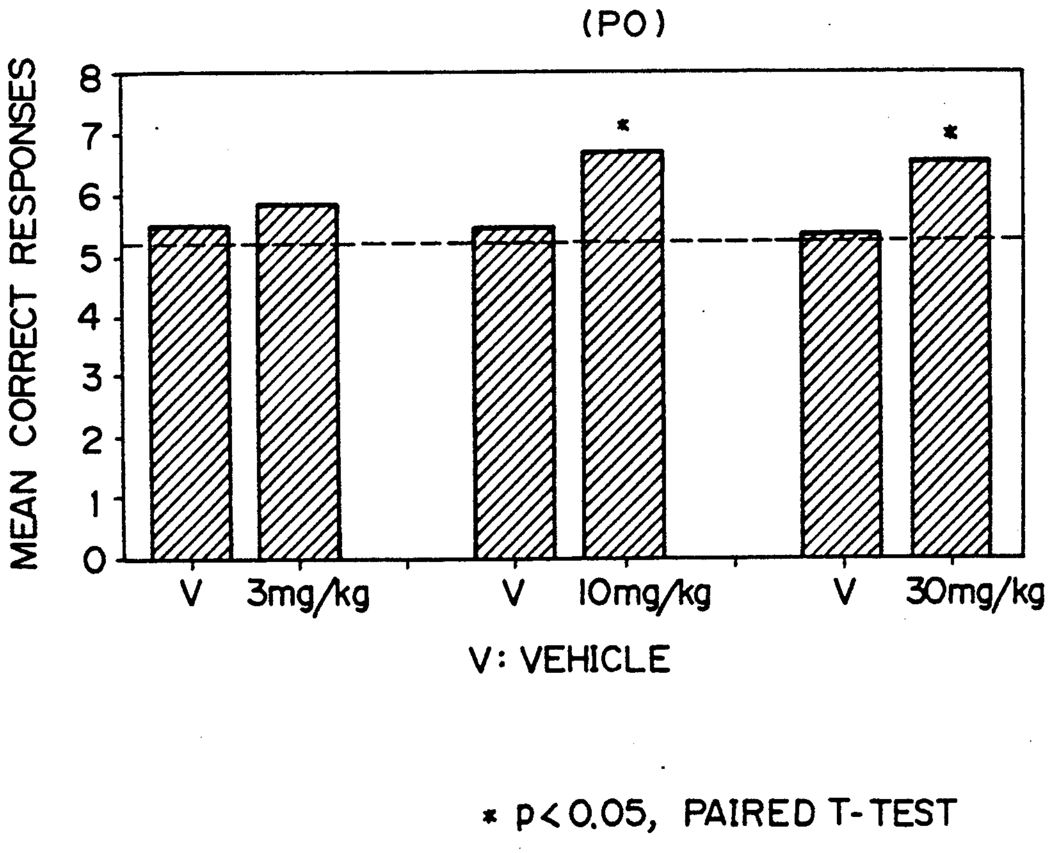
FIG. 1 shows mean correct response vs the dose of a compound of the present invention administered to rats under a radial-arm maze task in Test Example 6.

The compounds of the general formula (I) are novel and may be prepared by the following methods (a)-(h). the choice of which depends on $R_1$ in the general formula (I).

(a) If $R_1$ is a branched lower alkyl group or a cycloalkyl group substituted by a hydroxyl group, or if it is a lower alkyl group or a cycloalkyl group containing a carbonyl group, the following procedure is taken: a starting compound represented by the general formula (II):

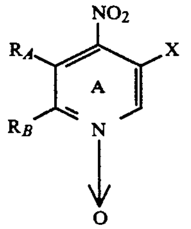

(II)

(where $R_A$ and $R_B$ each represents a hydrogen atom or, when taken together with the ring A, form a quinoline ring; X is a halogen) is reacted with an enamine corresponding to the end compound thereby introducing a substitute on both 2 and 3 positions, and subsequently the nitro group on 4 position is reduced, optionally followed by further reduction. The reaction with enamine is performed in an inert solvent such as chloroform or methylene chloride and the enamine to be used corresponds to the end compound as exemplified by 1-(N-morpholino)cyclohexene. The reaction temperature ranges from 20° to 80° C. and is preferably room temperature. The reduction of the nitro group on 4 position involves an ordinary reduction reaction and may be accomplished by hydrogenation in the presence of a catalyst such as palladium-on-carbon, Raney nickel or Raney cobalt. The reduction reaction is performed in an inert solvent such as tetrahydrofuran or an alcohol. A compound of the general formula (I) wherein $R_4$ and $R_5$ combine with the pyridine ring to form a 5,6,7,8-tetrahydroquinoline ring is obtained by performing further reduction in an acidic solvent such as trifluoroacetic acid or acetic acid in the presence of a reduction catalyst such as platinum dioxide or Raney nickel.

(b) If $R_1$ is a branched lower alkyl group or a cycloalkyl group, a compound of the general formula (II) is reacted with an enamine and the nitro group on 4 position is reduced as in (a). The resulting compound of the general formula (III):

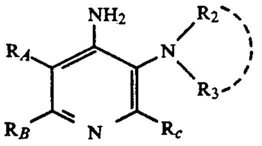

(III)

(where Rc is a lower alkyl group or a cycloalkyl group containing a carbonyl group; $R_A$, $R_B$, $R_2$ and $R_3$ are each the same as defined above) is reacted with a compound of the general formula Y—$NHNH_2$ (where Y is a paratoluenesulfonyl group or a hydrogen atom) in a solvent such as alcohol at 20°-80° C., preferably at room temperature. By subsequent reaction with a reducing agent such as $NaBH_4$, $LiAlH_4$ or $BH_3$, a compound of the general formula (I) is obtained. By performing further reduction which is optional, a 5,6,7,8-tetrahydroquinoline based end compound can be obtained.

(c) If $R_1$ is

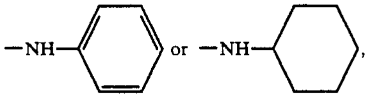

the following scheme may be employed:

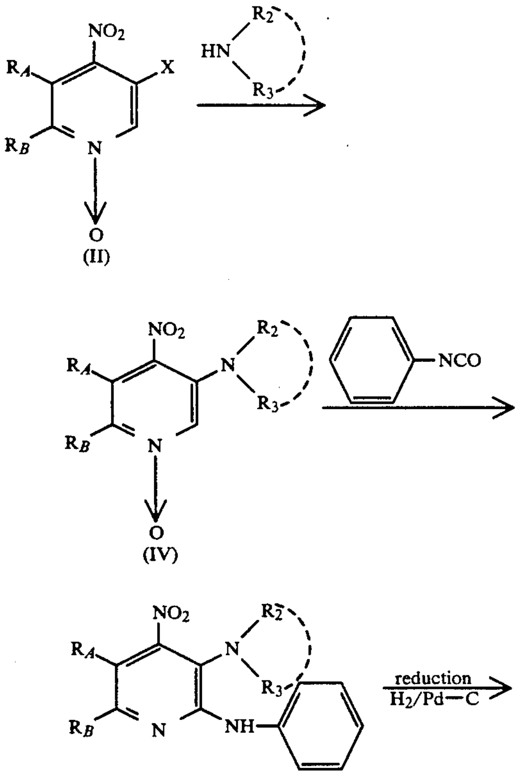

(II)

(IV)

(V)

-continued

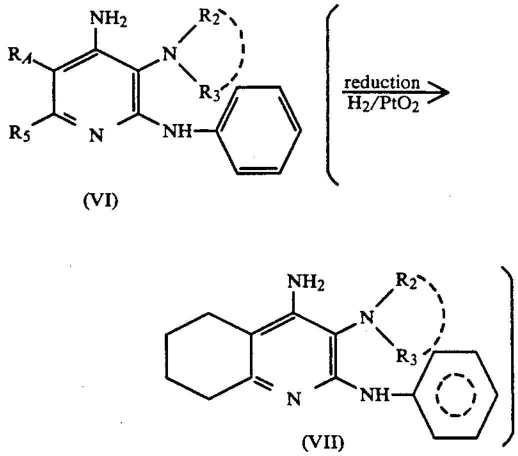

(VI)

(VII)

(where $R_2$, $R_3$, $R_A$, $R_3$ and X have the same meanings as defined above:

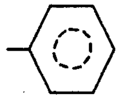

denotes a phenyl or cyclohexyl group).

The conversion from the general formula (II) to (IV) is carried out by reacting the compound (II) with a corresponding amine in an inert solvent such as tetrahydrofuran or an alcohol, preferably at room temperature. The conversion from the general formula (IV) to (V) is carried out using phenyl isocyanate in a solvent such as dimethylformamide or dimethyl acetamide. The reaction temperature is in the range of 50°-100° C., preferably 80° C. The conversion from the general formula (V) to (VI) involves an ordinary step of reduction and may be accomplished by hydrogenation in the presence of a catalyst such as palladium-on-carbon. Raney nickel or Raney cobalt. The reduction reaction is performed in an invert solvent such as tetrahydrofuran or an alcohol, preferably at room temperature. By further reducing the compound of the general formula (VI) with a suitable catalyst such as platinum dioxide or Raney cobalt, an end compound wherein $R_1$ is

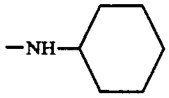

or a 5,6,7,8-tetrahydroquinoline based compound is obtained (general formula (VII)).

(d) If $R_1$ is —NH—RD (RD is a lower alkyl group), the following scheme may be employed:

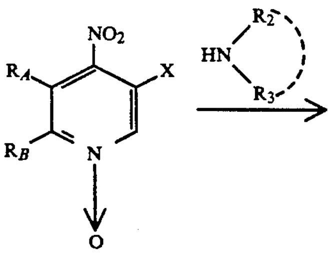

(II)

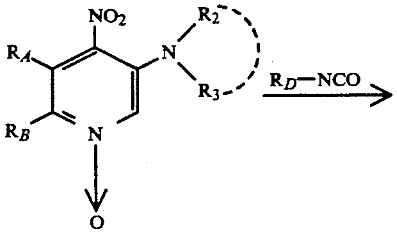

(IV)

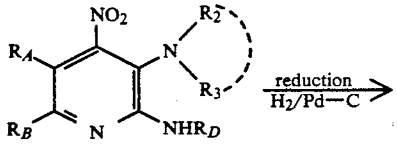

(VIII)

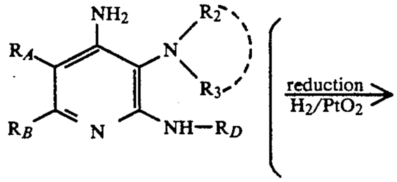

(IX)

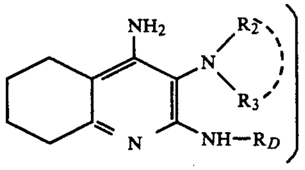

(X)

(where $R_2$, $R_3$, $R_A$, $R_B$, $R_D$ and X are the same as defined above).

The conversion from the general formula (II) to (IV) is carried out as in (c). The conversion from the general formula (IV) to (VIII) is carried out by reacting the compound of formula (IV) with RD—NCO (where RD is a lower alkyl group) in a sealed tube. The reaction is performed in an inert solvent such as dimethylformamide at 100°-150° C., preferably at 130° C., for a period of 4-10 hours, preferably 6 hours. Conversion from the general formula (VIII) to (IX) may be accomplished by reducing the nitro group as in (a)-(c). If desired further reduction may be performed by treatment with a suitable catalyst such as platinum dioxide or Raney cobalt and this leads to the production of an end compound of the general formula (X).

(e) If $R_1$ is a lower alkoxy group, the following scheme may be employed:

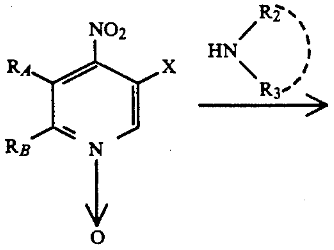

(II)

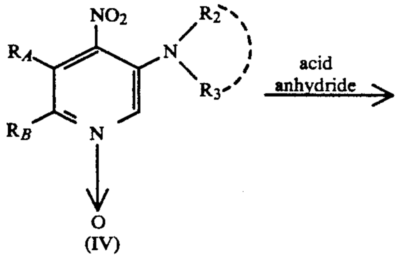

(IV)

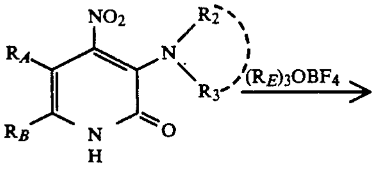

(XI)

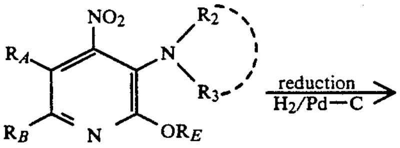

(XII)

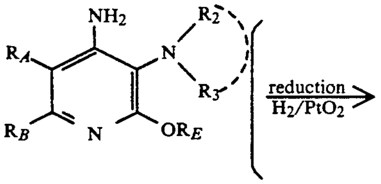

(XIII)

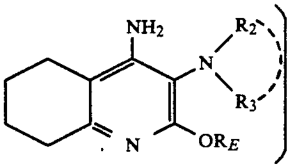

(XIV)

The conversion from the general formula (II) to (IV) is carried out as in (c). The conversion from the general formula (IV) to (XI) may be carried out in the usual manner and an α-oxy form (XI) can be obtained in high yield treatment with acetic anhydride in pyridine used as a solvent. The reaction is performed at a temperature in the range of 60°-100° C., preferably at 80° C., and is completed in 1-8 hours. This reaction may also be performed with p-toluenesulfonyl chloride or chloroform used as a solvent. Conversion from the general formula (XI) to (XII) is performed by reacting the compound of (XI) with $(R_E)_3OBF_4$ ($R_E$ is a lower alkyl group such as methyl or ethyl) or $AgBF_4$ $R_EX$ ($R_E$ has the same meaning as defined above) under cooling with ice in a nitrogen stream. The reaction is performed over 4–7 days in a solvent such as chloroform or methylene chloride. Conversion from the general formula (XII) to (XIII) and from (XIII) to (XIV) is performed by reduction reaction in the same manner as already described.

(f) If $R_1$ is a hydrogen atom, a linear lower alkyl group or a hydroxyl-substituted linear lower alkyl group, the following scheme may be employed:

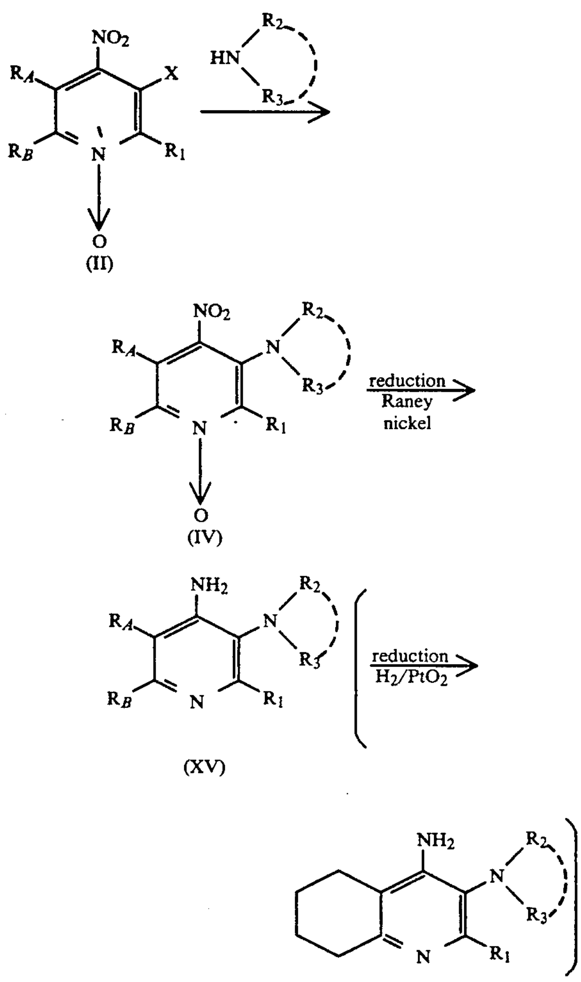

(II)
(IV)
(XV)
(XVI)

(where $R_2$, $R_3$, $R_A$, $R_B$ and X have the same meanings as defined above).

The conversion from the general formula (II) to (IV) is carried out as in (c). Conversion from the general formula (IV) to (XV) is accomplished by reduction reaction which is performed in the presence of a catalyst such as Raney nickel in a solvent such as tetrahydrofuran or an alcohol, preferably at room temperature. The reaction may also proceed in the presence of an iron catalyst in a solvent such as acetic acid or trifluoroacetic acid at a temperature of 90°–100° C. If desired further reduction may be performed with a suitable catalyst such as platinum dioxide, thereby producing an end compound of the general formula (XVI).

(g) If $R_1$ is a hydroxyl group, the following scheme may be employed:

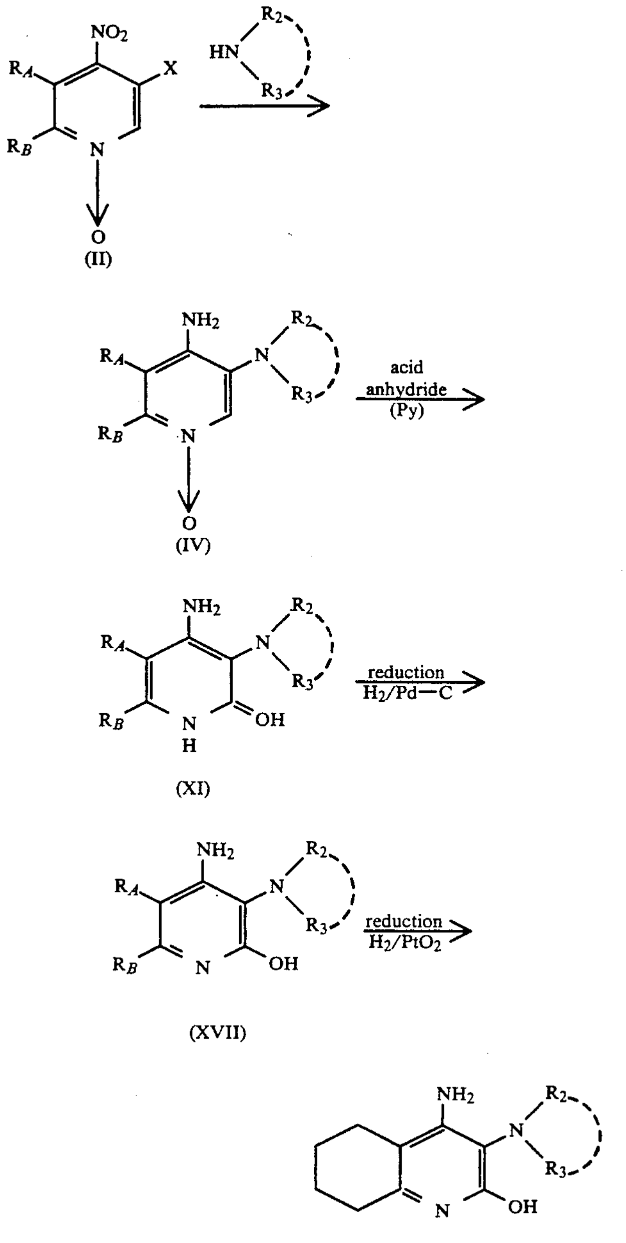

(II)
(IV)
(XI)
(XVII)
(XVIII)

(where $R_2$, $R_3$, $R_A$, $R_B$ and X have the same meanings as defined above).

The conversion from the general formula (II) to (IV) and from (IV) to (XI) is performed as described above. Conversion from the general formula (XI) to (XVII) is performed as already-described in connection with the reaction for reducing the nitro group and may be accomplished by reduction in the presence of a catalyst such as palladium-on-carbon or Raney nickel. If desired, further reduction may be performed to obtain an end compound represented by the general formula (XVIII).

(h) If $R_1$ is a morphlino group, the following scheme may be employed:

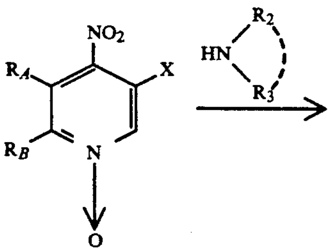

(II)

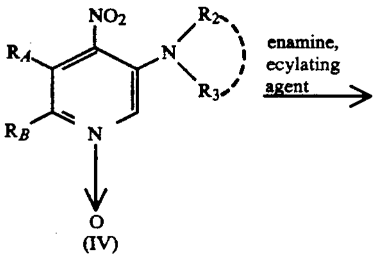

(IV)

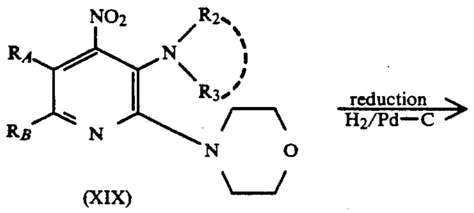

(XIX)

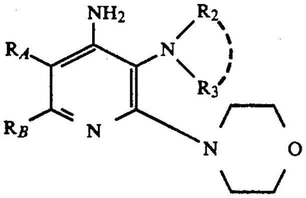

(where $R_2$, $R_3$, $R_A$, $R_B$ and X have the same meanings as defined above).

The conversion from the general formula (II) to (IV) is performed as in (C). Conversion from the general formula (IV) to (XIX) is performed by reaction with an enamine having a morpholino group such as 1-(N-morphlino)cyclohexene and an acylating agent such as benzoyl chloride, tosyl chloride or an acid anhydride such as acetic anhydride in an inert solvent such as chloroform or methylene chloride. The reaction temperature is in the range of 0°–10° C. and the reaction time is in the range of 3–24 hours, preferably 12 hours. The enamine is added in an amount of 1.5–3 equivalents, preferably 2 equivalents, and the acylating agent is added in an amount of 0.5–2 equivalents, preferably 1 equivalent.

Conversion from the general formula (XIX) to (XX) involves the usual practice of reduction as describe above and may be accomplished by hydrogenation in the presence of a catalyst such as palladium-on-carbon. Raney nickel or Raney cobalt.

The compounds of the general formula (I) thus obtained exhibit excellent activity in accelerating mnemonic and learning performance and improving the brain function in small doses and hence are useful as pharmaceutical drugs.

The compounds of the general formula (I) may be converted to acid addition salts as required. If such acid addition salts are to be used in medical applications, any pharmaceutically acceptable salt forming acids may be used. Specific examples include organic acids such as citric acid, fumaric acid, maleic acid and tartaric acid, and inorganic salts such as hydrochloric acid, hydrobromic acid, nitric acid and sulfuric acid.

The following examples and test examples are provided for the purpose of further illustrating the present invention but are in no way to be taken as limiting.

EXAMPLE 1

Preparation of 4-amino-3-morpholino-2-(2'-oxycyclohexyl)quinoline Compound No. 3):

(a) 3-Bromo-4-nitroquinoline-N-oxide (2.69 g, 0.01 mol) and 1-(N-morpholino)cyclohexene (4.18 g. 0.02B mol) were dissolved in B0 ml of chloroform and the mixture was stirred at room temperature for 4 days. After distilling off the chloroform under vacuum, the residue was subjected to extraction with benzene. Following washing with water and drying, the benzene was distilled off under vacuum and ethanol was added to the residue, whereupon crystal was precipitated. The resulting crystals were recrystallized from ethanol to obtain 3-morpholino-4-nitro-2-(2'-oxocyclohexyl)-quinoline in an amount of 2.g7 g (yield. 04g).

(b) 3-Morpholino-4-nitro-2-(2'-oxocyclohexyl)quinoline (2.00 g. 0.00B mol) was dissolved in tetrahydrofuran (10 ml) and subjected to reduction in the presence of 10g palladium-on-carbon (0.3 g). After completion of the reaction, the palladium-on-carbon catalyst was filtered off and the mother liquor was concentrated. Following purification by chromatography on an alumina column using chloroform as a developing solvent, recrystallization from ethanol was performed, whereupon 4-amino-3-morpholino-g-(2'-oxocyclohexyl)quinoline was obtained in an amount of 0.94 g (yield, 46%).

EXAMPLE 2

Preparation of 4-amino-g-(2.-hydroxycyclohexyl)-3-morpholino-5,6,7,8-tetrahydroquinoline (Compound No. 0):

The 4-amino-S-morpholino-2-(2'-oxocyclohexyl)-quinoline (0.8 g, 0.0024 mol) obtained in Example 1-(b) was dissolved in 10 ml of trifluoroacetic acid and subjected to reduction in the presence of platinum (IV) dioxide (0.g g). After completion of the reaction, the platinum dioxide was filtered off and the mother liquor was concentrated. Following purification by chromatography on an alumina column using chloroform as a developing solvent, recrystallization from benzene/n-hexane was performed, whereupon 4-amino-2-(2'-hydroxychlorohexyl)-3-morpholino-5,6,7,8-tetrahydroquinoline was obtained in an amount of 0.69 g (yield, 85%).

EXAMPLE 3

Preparation of 4-amino-2-cyclohexyl-3-morpholinoquinoline (Compound No. 18):

(a) The 4-amino-3-morpholino-2-(2'-oxocyclohexyl)-quinoline (1.0 g, 0.0031 mol) obtained in Example 1-(b) and p-toluenesulfonyl hydrazide (0.72 g, 0.0039 mol) were dissolved in 10 ml of methanol and the solution was stirred at room temperature for 4 hours, whereupon gradual crystallization occurred. The crystals were recovered by filtration under vacuum and washed with methanol to obtain 2-(4'-amino-3'-morpholinoquinolyl)-1-tosylhydrazonocyclohexane in an amount of 0.65 g (yield, 43%).

The 2-(4'-amino-3'-morpholinoquinolyl)-1-tosylhydrazonocyclohexane (0.65 g, 0.0013 mol) was suspended in methanol (30 ml) and 1.0 g of sodium borohydride was gradually added under cooling with ice. Thereafter, the mixture was heated under reflux on an oil bath for 5 hours. Methanol was distilled off from the whole reaction mixture under vacuum and the residue was subjected to extraction with chloroform. The chloroform layer was washed with water, dried with anhydrous sodium sulfate and subjected to isolation and purification steps on an alumina column, thereby obtaining 4-amino-2-cyclohexyl-3-morpholinoquinoline in an amount of 0.31 g (yield. 78%).

EXAMPLE 4

Preparation of 4-amino-2-cyclohexyl-3-morpholino-5,6,7,8-tetrahydroquinoline (Compound No. 10):

The 4-amino-cyclohexyl-S-morpholinoquinoline (0.31 g. 0.001 mol) obtained in Example 3-(b) was dissolved in 10 ml of trifluoroacetic acid and subjected to reduction in the presence of platinum (IV) dioxide (0.3 g). After completion of the reaction, the platinum dioxide was filtered off and the mother liquor was concentrated. Following purification by chromatography on an alumina column using chloroform as a developing solvent, recrystallization from benzene/n-hexane was performed, whereupon 4-amino-2-cyclohexyl-3-morpholino-5,6,7,8-tetrahydroquinoline was obtained in an amount of 0.25 g (yield, 83%).

EXAMPLE 5

Preparation of 4-amino-2-anilino-3-morpholinoquinoline (Compound No. 13):

(a) 3-Bromo-4-nitroquinoline-N-oxide (10 g, 0.037 mol) was dissolved in tetrahydrofuran and after adding morpholine (8.1 g. 0.093 mol). the mixture was stirred at room temperature, whereupon gradual crystallization occurred. Tetrahydrofuran was distilled off from the whole reaction mixture under vacuum and the residue was dissolved in chloroform. The chloroform layer was washed with water and dried with form under vacuum, the residue was washed with a small amount of ethanol and recovered by filtration under vacuum, whereupon 3-morpholino-4-nitroquinoline-N-oxide was obtained in an amount of 10 g (yield, 98%).

(b) The 3-morpholino-4-nitroquinoline-N-oxide (3 g, 0.011 mol) was suspended in dimethylformamide (40 ml) and following addition of phenyl isocyanate (3.4 g, 0.029 mol), the mixture was added on an oil bath at 80°-90° C. for ca. 3 hours. The reaction mixture was totally charged into water and subjected to extraction with chloroform. The chloroform layer was washed with water and dried with anhydrous sodium sulfate. After the chloroform was distilled off under vacuum, the residue was subjected to recrystallization with ethanol. The resulting crystal was recovered by filtration under vacuum to obtain 2-anilino-3-morpholino-4-nitroquinoline in an amount of 2.95 g (yield, 77%).

(c) The 2-anilino-3-morpholino-4-nitroquinoline (2.9 g, 0.0083 mol) was dissolved in tetrahydrofuran (10 ml) and subjected to reduction in the presence of 10g palladium-on-carbon (0.3 g). After completion of the reaction, the palladium-on-carbon catalyst was filtered off and the mother liquor was concentrated. Following purification by chromatography on an alumina column using chloroform as a developing solvent, recrystallization from methanol was conducted to obtain 4-amino-2-anilino-3-morpholinoquinoline in an amount of 1.89 g (yield, 69%).

EXAMPLE 6

Preparation of 4-amino-2-anilino-3-morpholino-5,6,7,8-tetrahydroquinoline (Compound No. 15):

The 4-amino-2-anilino-3-morpholinoquinoline (1.8 g, 0.0055 mol) obtained in Example 5-(c) was dissolved in trifluoroacetic acid (10 ml) and subjected to reduction in the presence of platinum (IV) dioxide (0.3 g). After completion of the reaction, platinum dioxide was filtered off and the mother liquor was concentrated. Following purification by chromatography on an alumina column using chloroform as a developing solvent, recrystallization from benzene was performed, whereupon 4-amino-2-anilino-3-morpholino-5,6,7,8-tetrahydroquinoline was obtained in an amount of 0.58 g (yield, 32%).

EXAMPLE 7

Preparation of 4-amino-2-ethylamino-3-morpholinoquinoline (Compound No. 43):

(a) The 3-morpholino-4-nitroquinoline-N-oxide (3 g, 0.011 mol) obtained in Example 5-(a) was dissolved in dimethylformamide (40 ml) and following the addition of ethyl isocyanate (2.7 g, 0.038 mol), the suspension was heated in a sealed tube on an oil bath at 130° C. for ca. 6 hours. The mixture was totally charged into water and subjected to extraction with chloroform. The chloroform layer was washed with water, dried with anhydrous sodium sulfate and concentrated under vacuum. Following isolation by chromatography on a silica gel column (solvent: 5% methanol/chloroform). recrystallization from ethanol was performed, whereupon 2-ethylamino-3-morpholino-4-nitroquinoline was obtained in an amount of 2.1 g (yield, 64%).

(b) The 2-ethylamino-3-morpholino-4-nitroquinoline (2.0 g, 0.0066 mol) was dissolved in tetrahydrofuran (10 ml) and subjected to reduction in the presence of 10g palladium-on-carbon (0.3 g). After completion of the reaction, the palladium-on-carbon catalyst was filtered off and the mother liquor was concentrated. Following purification by chromatography on an alumina column using chloroform as a developing solvent, recrystallization from ethanol gas conducted, whereupon 4-amino-2-ethylamino-3-morpholinoquinoline was obtained in an amount of 1.2 g (yield, 67%).

EXAMPLE 8

Preparation of 4-amino-2-ethoxy-3-morpholinoquinoline (Compound No. 38):

(a) The 3-morpholino-4-nitroquinoline-N-oxide (4 g, 0.015 mol) obtained in Example 5-(b) was dissolved in acetic anhydride (20 ml) and pyridine (20 ml) and the solution was heated on an oil bath at 80° C. for 3 hours. Excess acetic anhydride and pyridine were distilled off from the whole reaction mixture in vacuum and the residue was washed with ether to obtain 3-morpholino-4-nitro-2-quinolone in an amount of 3.5 g (yield, 88%), (b) The 3-morpholino-4-nitro-2-quinoline (3.5 g, 0.013 mol) was suspended in methylene chloride (200 ml). To the ice-cooled suspension, 25 ml of a solution of triethyl oxonium tetrafluoroborate in methylene chloride was added in a nitrogen stream and the mixture was stirred at room temperature for 7 days. The whole portion of the mixture was poured into 50% aqueous potassium carbonate and the resulting mixture was subjected to extraction with chloroform. The chloroform layer was washed with water and dried with anhydrous sodium sulfate. Upon isolation and purification by chromatography on a silica gel column (solvent: chloroform), 2-ethoxy-3-morpholino-4-nitroquinoline was obtained in an amount of 1.3 g (yield, 34%).

(c) The 2-ethoxy-3-morpholino-4-nitroquinoline (1.2 g, 0.004 mol) was dissolved in tetrahydrofuran (10 ml) and subjected to reduction in the presence of 10g palladium-on-carbon (0.3 g). After completion of the reaction, the palladium-on-carbon catalyst was filtered off and the mother liquor was concentrated. Following purification by chromatography on an alumina column using chloroform as a developing solvent, recrystallization from chloroform gas performed to obtain 4-amino-2-ethoxy-3-morpholinoquinoline in an amount of 0.7 g (yield, 60%).

EXAMPLE 9

Preparation of 4-amino-3-piperidino-2-(2'-oxocyclohexyl)quinoline (Compound No. 7):

(a) 3-Bromo-4-nitroquinoline-N-oxide (10 g, 0.037 mol) and 1-(N-piperidino)cyclohexene (15.4 g, 0.093 mol) were dissolved in chloroform (100 ml) and the solution was stirred at room temperature for 2 days. The chloroform was distilled off under vacuum and the residue was subjected to extraction with benzene. Following washing with water and drying, benzene was distilled off under vacuum and the residue was purified and isolated by chromatography on a silica gel column using chloroform as a developing solvent. By recrystallization from ethanol, 3-piperidino-4-nitro-2-(2'-oxocyclohexyl)quinoline was obtained in an amount of 9 g (yield, 68%).

(b) The 3-piperidino-4-nitro-2-(2'-oxocyclohexyl)-quinoline (8.5 g, 0.024 mol) was dissolved in tetrahydrofuran (50 ml) and subjected to reduction in the presence of 10g palladium-on-carbon (1.2 g). After completion of the reaction, the palladium-on-carbon catalyst was filtered off and the mother liquor was concentrated. Following purification by chromatography on an alumina column using chloroform as a developing solvent, recrystallization from ethanol was conducted to obtain 4-amino-3-piperidino-2-(2'-oxocyclohexyl)quinoline in an amount of 6.1 g (yield, 74%).

EXAMPLE 10

Preparation of 4-amino-2-hydroxy-3-morpholinoquinoline (Compound No. 27):

(a) The 3-morpholino-4-nitroquinoline-N-oxide obtained in Example 5-(a) was dissolved in acetic anhydride (16 ml) and pyridine (16 ml) and the solution was heated on an oil bath at 80° C. for 1 hour. Excess acetic anhydride and pyridine were distilled off under vacuum from the whole reaction mixture and the residue was dissolved in chloroform, followed by washing with 10% $NaHCO_3$. The insoluble matter was recovered by filtration under vacuum, dissolved in acetone and treated with charcoal. The chloroform layer was dried with anhydrous $Na_2SO_4$ and $CHCl_3$ was distilled off under vacuum. The residue was combined with the charcoal treated (insoluble) matter and washed with ethanol to obtain 2-hydroxy-3-morpholino-4-nitroquinoline in an amount of 3.5 g (yield, 44%).

(b) The 2-hydroxy-3-morpholino-4-nitroquinoline (1.5 g, 0.0054 mol) was dissolved in a mixed solvent of methanol and tetrahydrofuran and subjected to catalytic reduction in the presence of 10g palladium-on-carbon. After completion of the reaction, the palladium-on-carbon catalyst was filtered off and the mother liquor was concentrated. Following purification by chromatography on an alumina column using chloroform as a developing solvent, recrystallization from chloroform was conducted to obtain 4-amino-2-hydroxy-3-morpholinoquinoline in an amount of 0.9 g (yield, 63%).

EXAMPLE 11

Preparation of 4-amino-3-piperidinoquinoline (Compound No. 1):

(a) 3-Bromo-4-nitroquinoline-N-oxide (10 g, 0.037 mol) was dissolved in tetrahydrofuran (100 ml). To the solution, piperidine (7.9 g, 0.093 mol) was added and the mixture was stirred at room temperature until gradual crystallization occurred. Tetrahydrofuran was distilled off from the whole reaction mixture under vacuum and the residue was dissolved in chloroform. The chloroform layer was washed with water and dried with anhydrous sodium sulfate. After distilling off the chloroform under vacuum, the residue was washed with a small amount of ethanol and recovered by filtration under vacuum to obtain 4-nitro-3-piperidinoquinoline-N-oxide in an amount of 6.0 g (yield, 59%).

(b) The 4-nitro-3-piperidinoquinoline-N-oxide (4 g, 0.015 mol) was dissolved in a mixed solvent of methanol and tetrahydrofuran (50 ml) and subjected to catalytic reduction in the presence of purified Raney nickel (2 ml). Upon isolation and purification by chromatography on an alumina column (developing solvent: $CHCl_3$), 4-amino-3-piperidinoquinoline was obtained in an amount of 2.1 g (yield, 63%).

EXAMPLE 12

Preparation of 4-amino-3-ethylamino-2-morpholinoquinoline (Compound No. 52):

(a) 3-Bromo-4-nitroquinoline-N-oxide (10 g, 0.037 mol) was dissolved in tetrahydrofuran (100 ml). To the solution, ethylamine (5.96 g, 70% in $H_2O$) was added and the mixture was stirred at room temperature for 1 hour. Tetrahydrofuran was distilled off under vacuum from the whole reaction mixture and the residue was dissolved in chloroform. The chloroform layer was washed with water and dried with anhydrous sodium sulfate. Upon isolation and purification by chromatography on a silica gel column using chloroform as a developing solvent, 3-ethylamino-4-nitroquinoline-N-oxide was obtained in an amount of 5.4 g (yield, 62%).

(b) The 3-ethylamino-4-nitroquinoline-N-oxide (1 g, 0.004 mol) was dissolved in chloroform (15 mol). To the ice-cooled solution, 1-(N-morpholino)-cyclohexene (1.7 g) and benzoyl chloride (0.7 g) were added dropwise. The mixture was restored to room temperature and stirred overnight. Following addition of water, the mixture was stirred for about 1 hour and washed with water. Thereafter, the $CHCl_3$ layer was separated and dried with anhydrous $Na_2SO_4$. Upon isolation and purification by chromatography on a silica gel column using chloroform as a developing solvent. 3-ethylamino-2-morpholino-4-nitroquinoline was obtained in an amount of 0.7 g (yield, 54%).

(c) The 3-ethylamino-2-morpholino-4-nitroquinoline (0.7 g, 0.0023 mol) was dissolved in a mixed solvent of methanol and tetrahydrofuran (15 ml) and subjected to catalytic reduction in the presence of 10g palladium-on-carbon (0.3 g), thereby obtaining 4-amino-3-ethylamino-2-morpholinoquinoline in an amount of 0.5 g (yield, 79%).

The compounds prepared in Examples 1-12 and other compounds of the general formula (I) are characterized in Table 1 below, wherein "Q" in the "$R_4$, $R_5$"

column means that $R_4$ and $R_5$ taken together with the ring A form a quinoline ring; "T" means that $R_4$ and $R_5$ taken together with the ring A form a 5,6,7,8-tetrahydroquinoline ring; and "P" means that $R_4$ and $R_5$ each represents a hydrogen atom.

TABLE 1

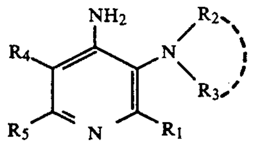

| Comp. No. | $R_1$ | $R_2$ | $R_3$ | $R_4.R_5$ | m.p. (°C.) | NMR | salt |
|---|---|---|---|---|---|---|---|
| 1 | H | | 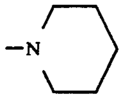 | Q | 255-257 | 1.36-2.27(6H,m), 2.72-3.26(4H,m), 5.32(2H,bs), 7.11-8.03(4H,m), 8.56(1H,s) | 2HCl |
| 2 | H | | 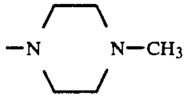 | Q | 113-114 | 2.32(3H,s), 2.35-3.20(8H,m), 5.30(2H,bs), 7.11-8.12(4H,m), 8.49(1H,s) | |
| 3 | 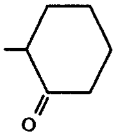 | | 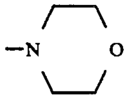 | Q | 195-196 | 1.50-2.87(8H,m), 3.01(4H,m), 3.79(4H,m), 4.12(1H,dd), 5.10(2H,bs), 7.15-8.05(4H,m) | |
| 4 | $-CH_2OH$ | H | H | Q | 242-244 | 3.41(1H,b), 4.85(2H,b), 5.11(2H,bs), 7.04-8.49(4H,m), 8.06(2H,bs) | |
| 5 | $-CH_2OH$ | H | $COCH_3$ | Q | 218-224 (dec.) | 2.08(3H,s), 3.26(1H,b), 4.46(2H,bs), 6.31(2H,bs), 7.05-8.30(4H,m), 8.86(1H,bs) | |
| 6 | 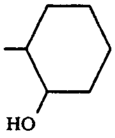 | | 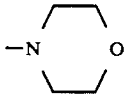 | T | 247-248 | 1.45-3.37(21H,m), 3.63-3.95(4H,m), 4.09(1H,s), 4.79(2H,bs), 7.50(1H,bs) | |
| 7 | 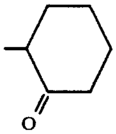 | | 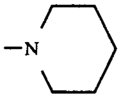 | Q | 192-194 | 1.50-1.90(6H,m), 1.90-2.80(8H,m), 2.80-3.25(4H,m), 4.12(1H,dd), 5.12(2H,bs), 7.15-8.05(4H,m) | |
| 8 | $-CH_3$ | | 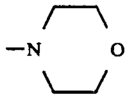 | Q | 270-280 (sublimable) | 2.87(3H,s), 2.90-4.44(8H,m), 5.10(2H,bs), 7.49-8.31(4H,m) | |
| 9 | 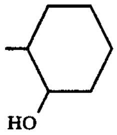 | | 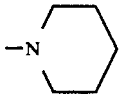 | T | 220-223 | 1.32-3.00(27H,m), 4.08(1H,s), 4.72(2H,bs), 7.56(1H,bs) | |
| 10 | $-CH_3$ | | 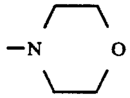 | T | 133-134 | 1.65-2.88(8H,m), 2.42(3H,s), 3.10-4.21(8H,m), 4.67(2H,bs) | |
| 11 | 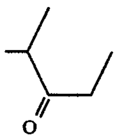 | | 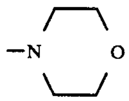 | Q | 205-208 | 0.98(3H, t), 1.51(3H,d), 2.17-2.59(2H,q), 2.66-3.98(8H,m), 3.92-4.39(1H,q), 5.35(2H,bs), 7.13-8.01(4H,m) | |

TABLE 1-continued
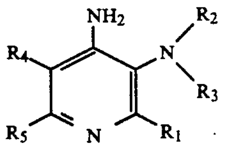
| Comp. No. | $R_1$ | $R_2$ | $R_3$ | $R_4.R_5$ | m.p. (°C.) | NMR | salt |
|---|---|---|---|---|---|---|---|
| 12 | 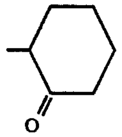 | | 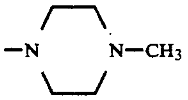 | Q | — | — | |
| 13 | 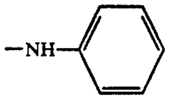 | | 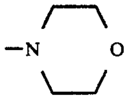 | Q | 224–225 | 2.51–3.79(4H,m), 3.70–4.11(4H,m), 5.59(2H,bs), 6.70–7.97(9H,m), 8.51(1H,bs) | |
| 14 | H | | 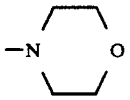 | Q | 168–170 | 2.21–3.15(4H,m), 3.16–4.07(4H,m), 5.30(2H,bs), 7.16–8.09(4H,m), 8.56(1H,s) | |
| 15 | 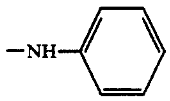 | | 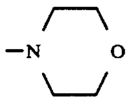 | T | 184–186 | 1.62–2.86(8H,m), 2.90–3.62(4H,m), 3.63–3.99(4H,m), 4.08(2H,bs), 6.66–8.01(6H,m) | |
| 16 | 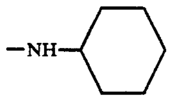 | | 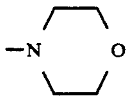 | T | 189–191 | 1.02–3.46(22H,m), 3.50–4.24(5H,m), 5.74(2H,bs), 6.69(1H,bs) | |
| 17 | H | | 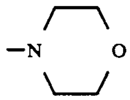 | T | 136–138 | 1.67–3.20(12H,m), 3.70–4.05(4H,m), 4.43(2H,bs), 7.92(1H,s) | |
| 18 | 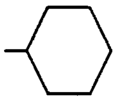 | | 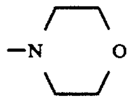 | Q | 195–196 | 1.11–2.12(10H,m), 2.53–4.25(9H,m), 5.30(2H,bs), 7.12–8.02(4H,m) | |
| 19 | 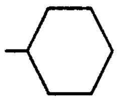 | | 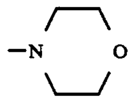 | T | 191–193 | 1.10–3.07(22H,m), 3.10–4.11(5H,m), 4.59(2H,bs) | |
| 20 | H | | 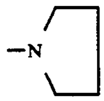 | Q | 263–264 (dec.) | 2.04–2.37(4H,m), 3.82–4.18(4H,m), 5.01(2H,bs), 7.35–8.51(5H,m) | |
| 21 | H | H | 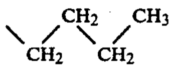 | Q | — | — | |
| 22 | 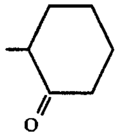 | $-CH_2-CH_3$ | $-CH_2-CH_3$ | Q | 192–193 | 1.02(6H,t), 1.50–2.90(8H,m), 2.80–3.31(4H,m), 5.17(2H,bs), 7.19–8.02(4H,m) | |

TABLE 1-continued
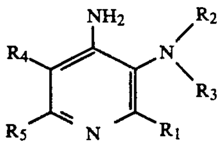
| Comp. No. | $R_1$ | $R_2$ | $R_3$ | $R_4.R_5$ | m.p. (°C.) | NMR | salt |
|---|---|---|---|---|---|---|---|
| 23 | 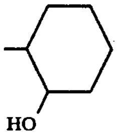 | $-CH_2-CH_3$ | $-CH_2-CH_3$ | T | 123–125 | 1.01(6H,t), 1.20–3.38(21H,m), 4.02(1H,s), 4.70(2H,bs), 7.75(1H,bs) | |
| 24 | 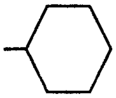 | $-CH_2-CH_3$ | $-CH_2-CH_3$ | Q | 280–285 (dec.) | 1.03(6H,t), 1.20–3.70(15H,m), 5.23(2H,bs), 7.20–8.00(4H,m) | HCl |
| 25 | 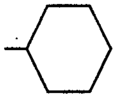 | $-CH_2-CH_3$ | $-CH_2-CH_3$ | T | 265–270 (sublimable) | 1.01(6H,t), 1.10–3.35(22H,m), 3.40–3.86(1H,m), 4.57(2H,bs) | |
| 26 | 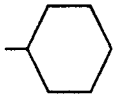 | | 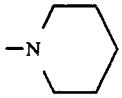 | Q | 131–132 | 1.09–2.47(16H,m), 2.64–3.39(5H,m), 5.30(2H,bs), 7.06–7.97(4H,m) | |
| 27 | $-OH$ | | 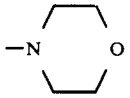 | Q | 283–284 | 2.91–4.20(8H,m), 6.11(2H,bs), 6.72–8.05(4H,m), 11.15(1H,bs) | |
| 28 | 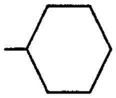 | | 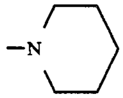 | T | 144–146 | 1.01–3.45(28H,m), 4.20–4.51(1H,m), 5.30(2H,bs) | |
| 29 | 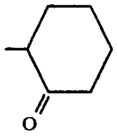 | $-CH_2CH_2CH_3$ | $-CH_2CH_2CH_3$ | Q | 176–177 | 0.64–1.10(6H,m), 1.10–3.40(6H,m), 3.85–4.30(1H,dd), 5.18(2H,bs), 7.13–8.07(4H,m) | |
| 30 | 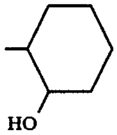 | $-CH_2CH_2CH_3$ | $-CH_2CH_2CH_3$ | T | 123–124 | 0.52–1.10(6H,m), 1.20–3.25(26H,m), 4.11(1H,bs), 6.72(2H,bs) | |
| 31 | 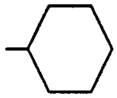 | $-CH_2CH_2CH_3$ | $-CH_2CH_2CH_3$ | Q | 129–130 | 0.67–1.03(6H,m), 1.10–2.30(14H,m), 2.60–3.35(5H,m), 5.22(2H,bs), 7.03–7.99(4H,m) | |
| 32 | 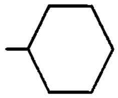 | $-CH_2CH_2CH_3$ | $-CH_2CH_2CH_3$ | T | 119–120 | 0.71–1.05(6H,m), 1.10–2.57(22H,m), 2.60–3.23(5H,m), 4.52(2H,bs) | |
| 33 | 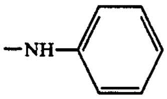 | $-CH_2CH_3$ | $-CH_2CH_3$ | Q | 153–155 | 0.88–1.27(6H,t), 2.95–3.30(4H,q), 3.97(1H,bs), 4.46(2H,bs), 6.75–8.28(9H,m) | |

TABLE 1-continued
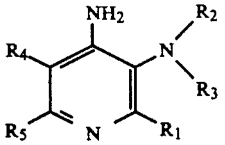
| Comp. No. | R1 | R2 | R3 | R4.R5 | m.p. (°C.) | NMR | salt |
|---|---|---|---|---|---|---|---|
| 34 | 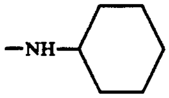 | $-CH_2CH_3$ | $-CH_2CH_3$ | T | 224–226 | 1.04–(6H,t), 1.51–2.03(4H,m), 2.12–2.84(4H,m), 2.97–3.65(4H,q), 7.20–8.35(7H,m), 12.97(1H,bs) | 2HCl |
| 35 | 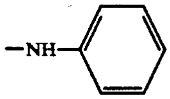 | | 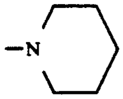 | Q | 119–121 | 1.34–2.06(6H,m), 2.77–3.34(4H,m), 4.49(2H,bs), 6.78–8.06(9H,m), 8.33(1H,bs) | |
| 36 | 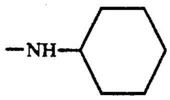 | | 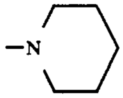 | T | 270 (dec.) | 1.69–3.21(24H,m), 3.62–4.22(6H,m), 4.41–4.58(1H,m), 7.84(1H,b) | 2HCl |
| 37 | 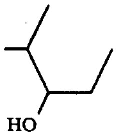 | | 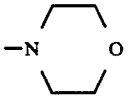 | T | 215–218 | 0.98(3H,t), 2.39(3H,d), 1.60–4.36(21H,m), 4.61(2H,bs) | HCl |
| 38 | $-OCH_2CH_3$ | | 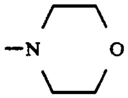 | Q | 149–151 | 1.45(3H,t), 2.32–4.09(2H,m), 4.33–4.68(2H,q), 5.19(2H,bs), 7.03–7.75(4H,m) | |
| 39 | 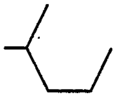 | | 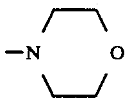 | Q | 132–134 | 0.65–2.20(10H,m), 2.61–4.22(9H,m), 5.29(2H,bs), 7.25–8.01(4H,m) | |
| 40 | 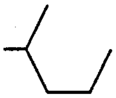 | | 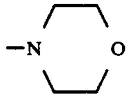 | T | 178–179 | 0.67–1.12(3H,m), 1.30–1.55(3H,d), 1.61–4.16(21H,m), 6.82(2H,bs) | |
| 41 | 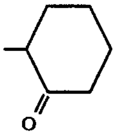 | | 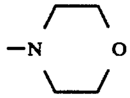 | T | 137–140 | 1.54–3.33(20H,m), 3.60–4.05(5H,m), 4.47(2H,bs) | |
| 42 | $-OCH_2CH_3$ | $-CH_2CH_3$ | $-CH_2CH_3$ | Q | 167–169 (dec.) | 1.08(6H,t), 1.47(3H,t), 3.31(4H,q), 4.83(2H,q), 7.12–7.89(4H,m), 8.10(2H,bs) | |
| 43 | $-NHCH_2CH_3$ | | 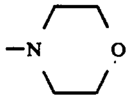 | Q | 152–153 | 1.24(3H,t), 2.61–3.93(10H,m), 5.44(2H,bs), 5.65(1H,bs), 6.81–7.89(4H,m) | |
| 44 | $-OCH_2CH_3$ | | 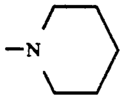 | Q | 168–170 | 1.40–2.06(9H,m), 2.10–3.61(4H,m), 4.63–5.03(4H,q), 6.96–7.72(4H,m), 8.11–8.5(2H,m) | |

TABLE 1-continued

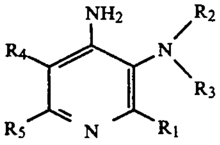

| Comp. No. | $R_1$ | $R_2$ | $R_3$ | $R_4.R_5$ | m.p. (°C.) | NMR | salt |
|---|---|---|---|---|---|---|---|
| 45 | $-NHCH_2CH_3$ | | 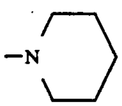 | Q | 99-100 | 1.29(3H,t), 1.30-2.18(6H,m), 2.71-3.35(4H,m), 3.30-4.11(2H,m), 4.25-4.92(2H,bs), 5.21-5.70(1H,b), 6.80-7.99(4H,m) | |
| 46 | $-NHCH_2CH_3$ | | 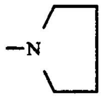 | Q | 99-101 | 1.23(3H,t), 1.84-2.31(4H,m), 3.02-3.38(4H,m), 3.38-3.87(2H,m), 4.44(2H,bs), 5.10(1H,m), 6.82-7.78(4H,m) | |
| 47 | $-OCH_2CH_3$ | $-COCH_3$ | $-CH_2CH_3$ | Q | 117-119 | 1.10(3H,t), 1.34(3H,t), 1.82(3H,s), 3.43-3.89(2H,m), 4.25-4.69(2H,q), 4.99(2H,bs), 7.05-7.84(4H,m) | |
| 48 | 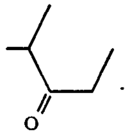 | | 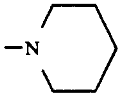 | Q | 205-207 | 0.80-1.15(3H,m), 1.21-2.06(10H,m), 2.54-3.53(4H,m), 3.67-4.12(2H,m), 6.52-6.98(2H,bs), 6.99-8.67(4H,m) | |
| 49 | 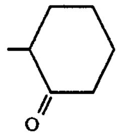 | | 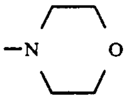 | P | 175-176 | 1.10-2.80(8H,m), 2.94(4H,m), 3.72(4H,m), 3.91(1H,dd), 6.34-8.00(2H,ABq) | |
| 50 | 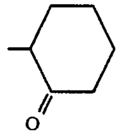 | | 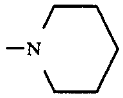 | P | 154-155 | 1.30-1.81(6H,m), 1.81-2.70(8H,m), 2.70-3.20(4H,m), 3.94(1H,dd) 4.51(2H,bs), 6.33-8.00(2H,ABq) | |
| 51 | 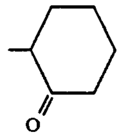 | $-CH_2CH_3$ | $-CH_2CH_3$ | P | 146-147 | 1.00(6H,t), 1.35-2.66(8H,m), 2.86(4H,q), 3.85(1H,dd), 4.53(2H,bs), 6.31-8.04(2H,ABq) | |
| 52 | 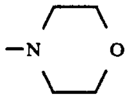 | H | $-CH_2CH_3$ | Q | 89-90 | 1.19(3H,t), 1.57-2.20(4H,m), 2.51-2.90(4H,m), 4.10-4.91(5H,m), 7.00-8.45(4H,m) | |

(dec.) denotes decomposition point.

Test Example 1

Inhibition of Acetylcholinesterase Activity:

Acetylcholinesterase activity was assayed in accordance with the method of S. H. Sterri and F. Fonnum described in European Journal of Biochemistry, 91: 215-222, 1978. The method consisted of incubating 0.5 $\mu$U of authentic acetylcholinesterase (ECS, 1,1,7) (Sigma, No. C-2888) at 30° C. for 15 minutes in a 20 mM sodium phosphate buffer (pH 7.4). with 1.3 mM $[1-{}^{14}C]$ acetylcholine (0.025 $\mu$Ci) being used as a substrate. Selected compounds of the general formula (I) were added at a concentration of 1 $\mu$M to the reaction solution and the resulting effect on enzymatic activity was evaluated.

The result was obtained as the average of three measurements and shown in Table 2 in terms of percentage, with the activity for the case where no drum compound was added being taken as 100.

TABLE 2
| Compound No. | Structure | Concentration | Inhibition rate (%) |
|---|---|---|---|
| None | — | — | 100 |
| 2 | 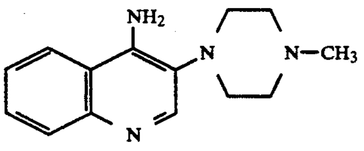 | 1 μM | 27.1 |
| 6 | 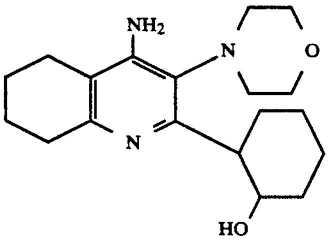 | 1 μM | 36.9 |
| 7 | 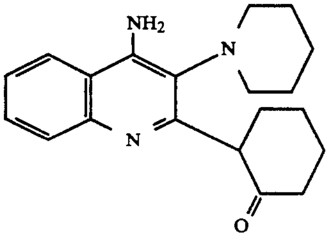 | 1 μM | 38.1 |
| 9 | 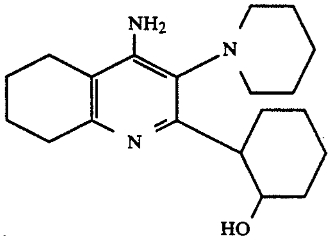 | 1 μM | 38.8 |
| 15 | 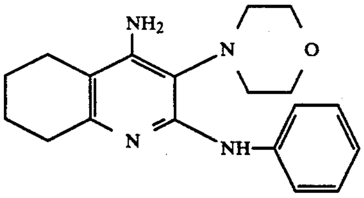 | 1 μM | 37.2 |
| 16 | 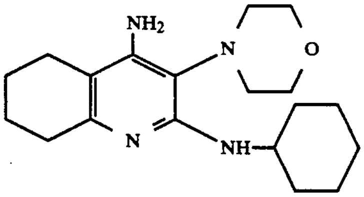 | 1 μM | 25.9 |
| 19 | 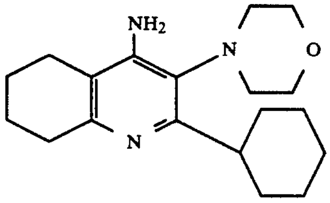 | 1 μM | 21.8 |

TABLE 2-continued

| Compound No. | Structure | Concentration | Inhibition rate (%) |
|---|---|---|---|
| 25 | 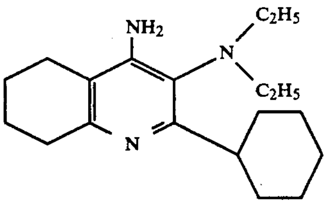 | 1 μM | 30.1 |
| 28 | 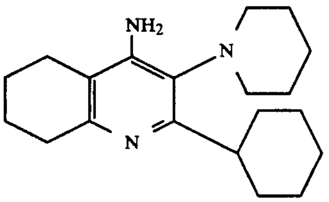 | 1 μM | 22.2 |
| 32 | 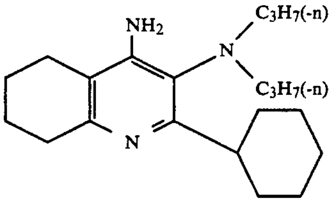 | 1 μM | 28.7 |
| 35 | 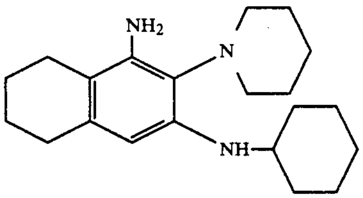 | 1 μM | 28.3 |
| 41 | 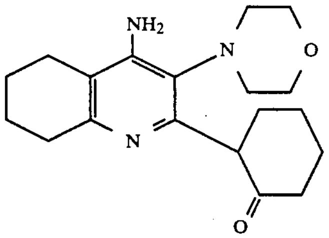 | 1 μM | 4.2 |

As Table 2 shows, the tested compounds of the present invention have a strong power to inhibit acetylcholin-esterase activity and hence are expected to stimulate the cholinergic function of the central nervous system. This will justify the anticipation that the compounds of the general formula (I) according to the present invention will be useful in the treatment of dementia of Alzheimer type which is accomplished by an observable damage specific to central cholinergic neurons (P. J. Whitehouse et al., Science, 215, 1237-1239, 1982).

Test Example 2

Inhibition of Catecholamine Uptake:

A crude synaptosomal fraction (P2) was obtained from the brain of rats (F344/$C_{rj}$) in the usual manner. In accordance with the method of S. H. Snyder and J. T. Coyle described in Journal of Pharmacology and Experimental Therapeutics, 165(1), 78-86, 1969, the fraction P2 was incubated in a Krebs-Henseleit bicarbonate buffer solution at 37° C. for 10 minutes together with 50 nM $^3$H-norepinephrine (0.25 jμCi). Thereafter, the uptake of norepinephrine into the synaptosomes was measured by the filtration method. Selected compounds were added at a concentration of 1 μM to the solution being incubated and their effect on norepinephrine uptake was examined. The control drug was tetrahydroaminoacridine (THA).

The results are shown in Table 3 in terms of percentage, with norepinephrine uptake in the absence of drug compounds being taken as 100.

TABLE 3

| Compound No. | Structure | Concentration | Inhibition rate (%) |
|---|---|---|---|
| None | — | — | 100 |

TABLE 3-continued
| Compound No. | Structure | Concentration | Inhibition rate (%) |
|---|---|---|---|
| 1 | 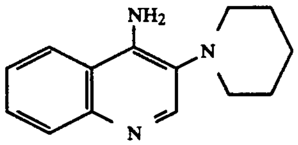 | 1 μM | 69.1 |
| 6 | 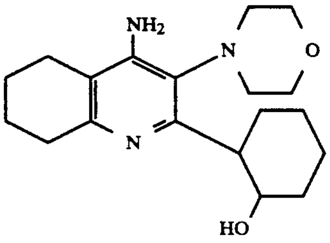 | 1 μM | 82.6 |
| 7 | 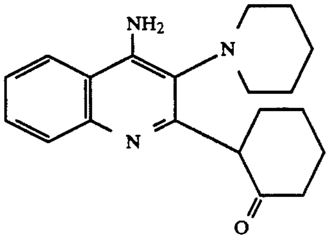 | 1 μM | 79.0 |
| 9 | 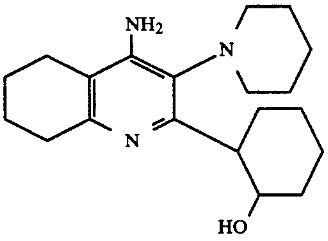 | 1 μM | 69.4 |
| 15 | 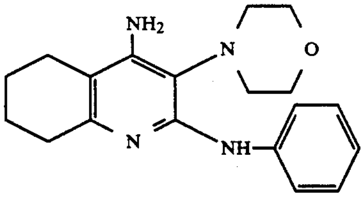 | 1 μM | 85.4 |
| 16 | 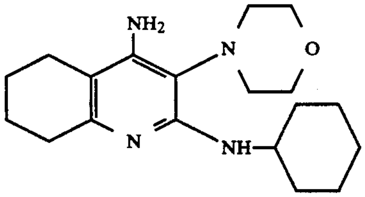 | 1 μM | 88.1 |
| 19 | 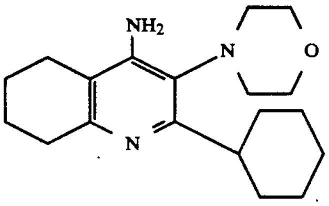 | 1 μM | 83.2 |

TABLE 3-continued
| Compound No. | Structure | Concentration | Inhibition rate (%) |
| --- | --- | --- | --- |
| 23 | 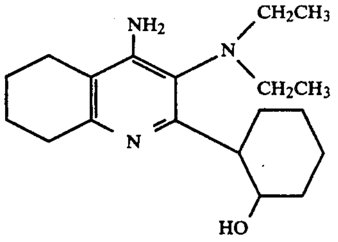 | 1 μM | 73.7 |
| 24 | 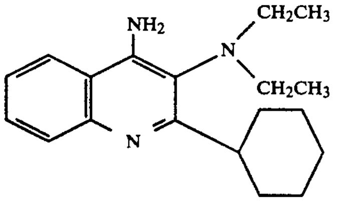 | 1 μM | 68.2 |
| 25 | 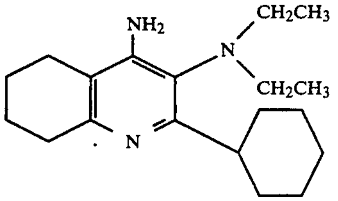 | 1 μM | 75.3 |
| 26 | 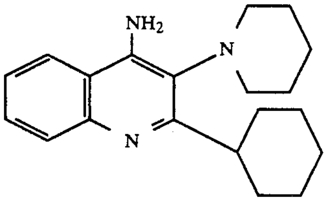 | 1 μM | 68.2 |
| 28 | 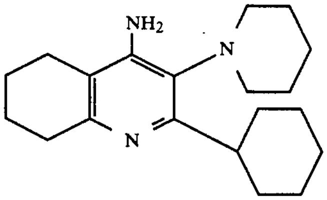 | 1 μM | 85.2 |
| 30 | 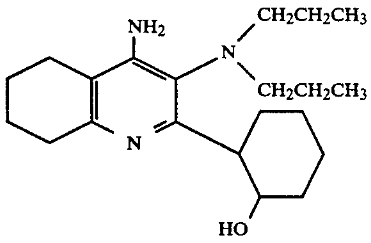 | 1 μM | 76.9 |
| 32 | 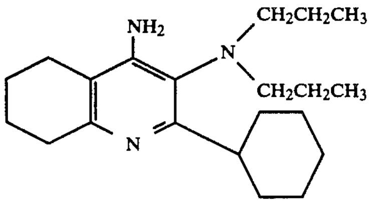 | 1 μM | 73.2 |

TABLE 3-continued

| Compound No. | Structure | Concentration | Inhibition rate (%) |
|---|---|---|---|
| 34 | 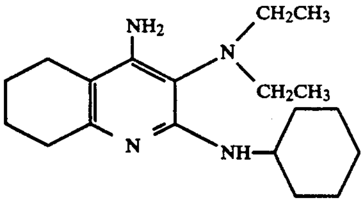 | 1 μM | 80.0 |
| 39 | 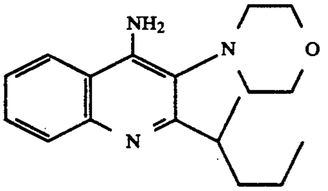 | 1 μM | 71.9 |
| 43 | 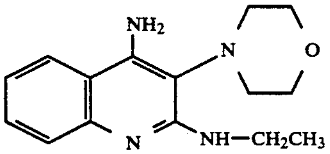 | 1 μM | 78.8 |
| 45 | 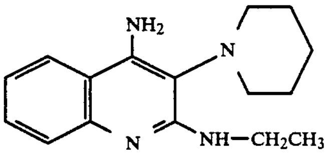 | 1 μM | 79.8 |
| 52 | 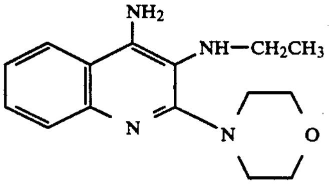 | 1 μM | 79.8 |
| control | 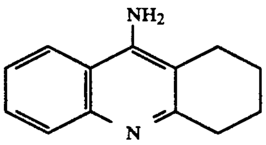 | 1 μM | 84.6 |

As Table 3 shows, in most of the cases examined, the tested compounds of the present invention exhibited a stronger activity than THA which is known as an effective drug against senile dementia. This result shows that the compounds of the present invention have a strong power to stimulate catecholaminergic neurons in the central nervous system, thus clearly demonstrating their utility as drugs in the treatment of neural and mental disorders.

Test Example 3

Improvement of memory and Learning Ability Tested by Passive Avoidance Response:

Four groups of male ICR mice (10–14 weeks old). each consisting of 10 animals, were used in the experiment. Except for one control group, the mice were administered with selected compounds of the present invention. The experimental chamber consisted of a light and a dark compartment and an electric current shock source was connected to the floor grid in the dark compartment.

The experimental sessions consisted of acclimation. acquisition, and retention trials and were performed for B days, one trial per day. In the acclimation trial, animals were placed in the light compartment of the experimental chamber and left there for 5 minutes to acclimate them to the apparatus. In the acquisition trial which was conducted on the 2nd day, the animals were placed in the light compartment and when they entered the dark compartment, they were confined and given an a.c. electric shock (1 mA) through the floor grid for 10 seconds. In the retention trial which was conducted 24 hours after the acquisition trial, the animals were placed in the light compartment of the chamber and the step-through latency (i.e., the time required for the animals to enter the dark compartment) was measured. A physiological saline solution was administered at the acclimation trial to all of the animals. At the acquisition trial, selected compounds were administered in amounts of 10 μg/kg of body weight (1 ml/100 g). The control group was administered the same amount of physiological saline solution 60 minutes before the start of the trial. All administrations were intraperitoneal.
The results are shown in Table 4 below.
TABLE 4
| Compound No. | Structure | dose (μ/kg i.p.) | Step through latency (sec) |
|---|---|---|---|
| None | — | — | 41.9 ± 10.2 |
| 2 | 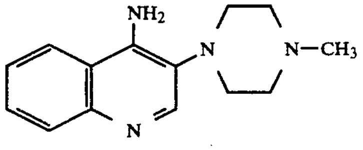 | 10 | 92.1 ± 13.5 |
| 6 | 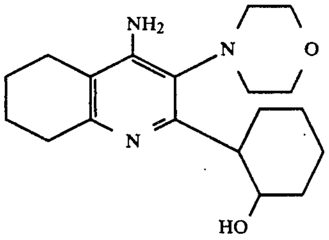 | 10 | 144.8 ± 45.1 |
| 7 | 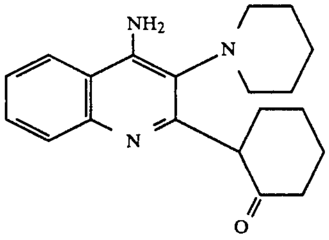 | 10 | 104.1 ± 28.5 |
| 9 | 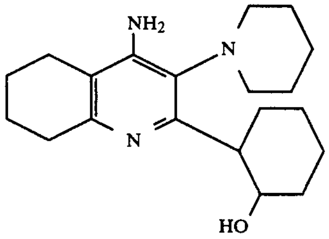 | 10 | 54.4 ± 7.2 |
| 13 | 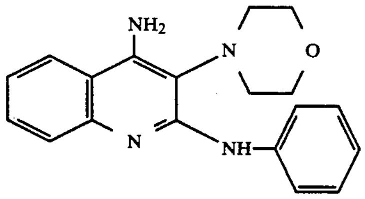 | 10 | 100.2 ± 17.8 |
| 15 | 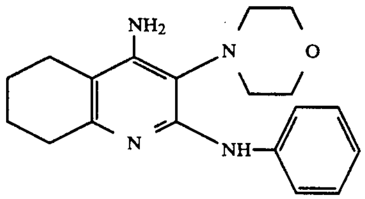 | 10 | 80.4 ± 14.6 |

TABLE 4-continued
| Compound No. | Structure | dose (μ/kg i.p.) | Step through latency (sec) |
|---|---|---|---|
| 16 | 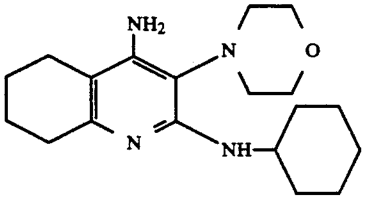 | 10 | 102.1 ± 22.3 |
| 18 | 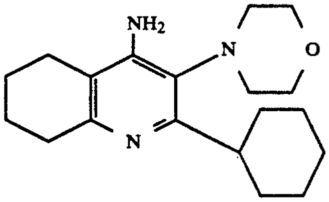 | 10 | 116.4 ± 29.2 |
| 19 | 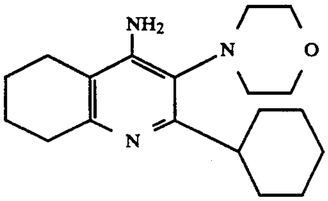 | 10 | 107.1 ± 29.9 |
| 22 | 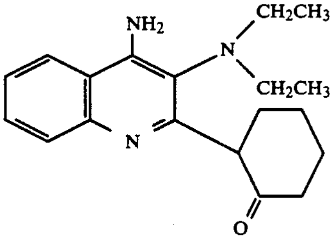 | 10 | 144.8 ± 25.5 |
| 24 | 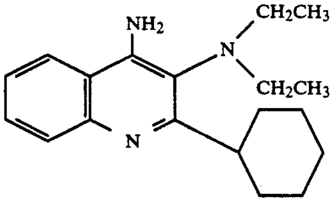 | 10 | 94.2 ± 14.7 |
| 32 | 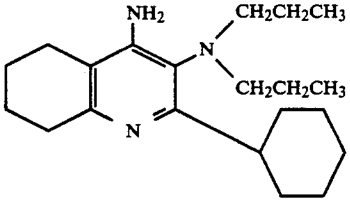 | 10 | 109.7 ± 16.6 |
| 39 | 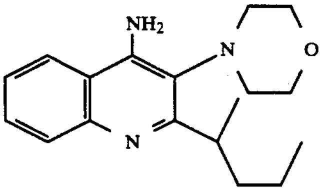 | 10 | 108.3 ± 16.0 |

TABLE 4-continued

| Compound No. | Structure | dose (μ/kg i.p.) | Step through latency (sec) |
|---|---|---|---|
| 40 | 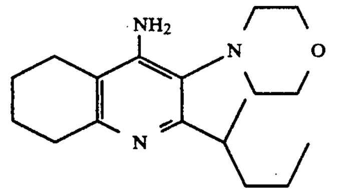 | 10 | 113.1 ± 29.6 |
| 43 | 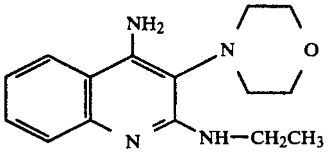 | 10 | 109.1 ± 13.4 |
| 44 | 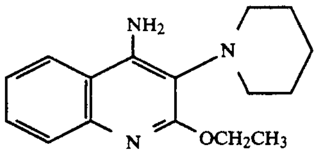 | 10 | 90.4 ± 12.4 |
| 45 | 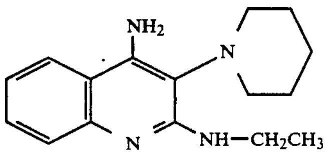 | 10 | 70.7 ± 6.8 |
| 50 | 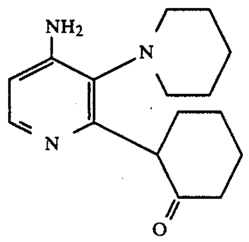 | 10 | 83.4 ± 14.8 |

As Table 4 shows, the step-through latency of the control group which was $41.9 \pm 10.2$ jwas significantly delayed by the tested compounds of the present invention, which hence were found to be effective in promoting memory and learning performance.

Test Example 4

Inhibition of Catecholamine Uptake:

The uptake of dopamine into synaptosomes was measured by repeating the procedure of Test Example 2 except that 50 nM $^3$H-norepinephrine (0.25 μCi) was replaced by 15 nM $^3$H-dopamine (0.68 μCi). The control drug was tetrahydroaminoacridine (THA). The result is shown in Table 5 in terms of percentage, with dopamine uptake in the absence of drugs being taken as 100.

TABLE 5

| Compound No. | Structure | Concentration | Inhibition rate (%) |
|---|---|---|---|
| None | — | — | 100 |
| 7 | 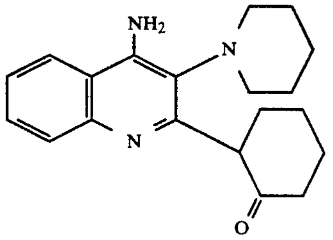 | 1 μM | 86.4 |

TABLE 5-continued
| Compound No. | Structure | Concentration | Inhibition rate (%) |
|---|---|---|---|
| 9 | 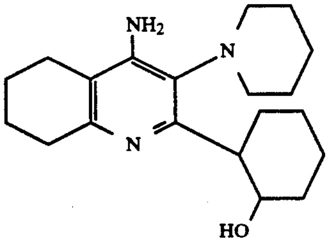 | 1 μM | 78.6 |
| 23 | 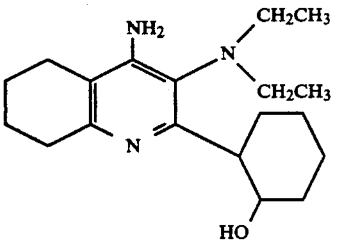 | 1 μM | 83.0 |
| 24 | 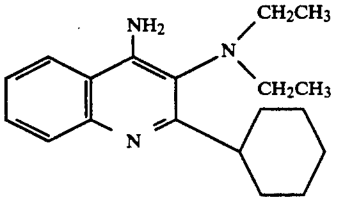 | 1 μM | 59.6 |
| 25 | 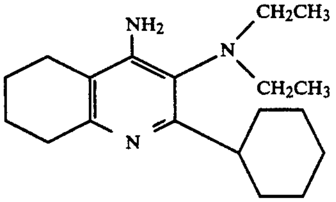 | 1 μM | 76.4 |
| 26 | 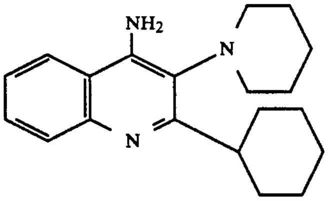 | 1 μM | 55.4 |
| 28 | 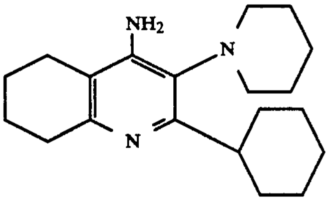 | 1 μM | 80.5 |
| 30 | 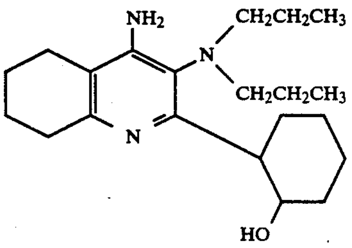 | 1 μM | 79.2 |

TABLE 5-continued

| Compound No. | Structure | Concentration | Inhibition rate (%) |
|---|---|---|---|
| 32 | 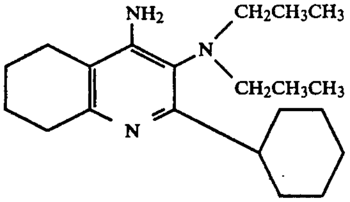 | 1 μM | 71.0 |
| 34 | 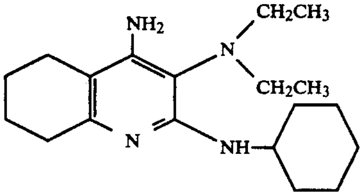 | 1 μM | 84.8 |
| 45 | 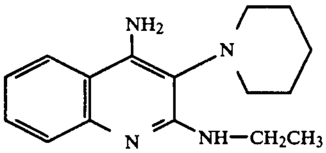 | 1 μM | 82.3 |
| 49 | 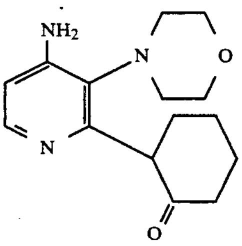 | 1 μM | 67.5 |
| 52 | 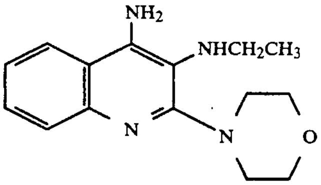 | 1 μM | 57.8 |
| control | 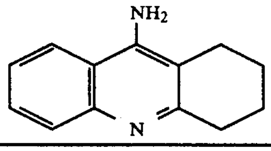 | 1 μM | 91.5 |

As Table 5 shows, the tested compounds of the present invention had a stronger activity than THA indicating together with the results shown in Test Example 2 their great ability to stimulate catecholaminergic neurons in the central nervous system. The compounds of the present invention are therefore anticipated to prove useful as a drug in the treatment of neural and mental disorders.

Test Example 5

Inhibition of Monoamine Oxidase (MAO):

A crude synaptosomal fraction (P2) was obtained from the brain of rats (F344/$C_{rj}$) in the usual manner and homogenized to perform MAO activity measurements. The substrate was 12 μM [$^{14}$C]-serotonin in the case of MAO-A activity measurements, and 5 μM [$^{14}$C]-2-phenethylamine in the case of MAO-B activity measurements. In accordance with the method of R. J. Wurtman and J. Axelrod described in Biochemical Pharmacol. 12, 1489-1440, 1963, the homogenates were incubated in 100 mM phosphate buffer (pH 7.4) at 37° C. for 20 minutes and the effect of adding selected compounds at a concentration of 10 μM was evaluated. The results are shown in Table 8.

TABLE 6

| Compound No. | Structure | Concentration | Inhibition rate (%) MAO-A | MAO-B |
|---|---|---|---|---|
| None | — | — | 100 | 100 |
| 1 | 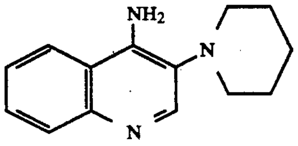 | 10 μM | 44.1 | 82.9 |
| 7 | 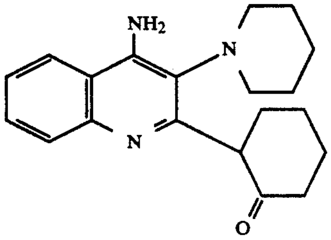 | 10 μM | 58.7 | 87.5 |
| 9 | 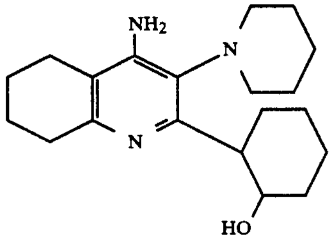 | 10 μM | 59.4 | 89.4 |
| 49 | 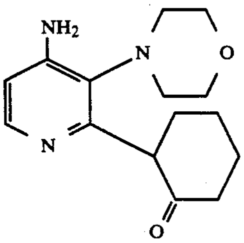 | 10 μM | 54.5 | 71.2 |
| 52 | 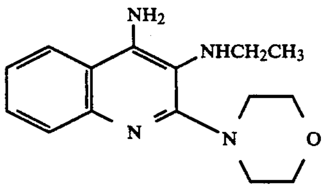 | 10 μM | 0.0 | 63.0 |
| control | 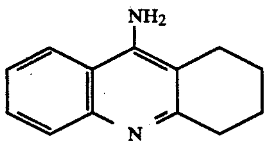 | 10 μM | 60.8 | 90.3 |

As Table 6 shows, the tested comPounds of the present invention were capable of inhibiting both MAO-A and MAO-B. with their ability to inhibit MAO-A being particularly great. Therefore, the compounds of the present invention are anticipated to exhibit stimulatory effect on monoaminergic neurons in the central nervous system, thereby proving useful in the treatment of neural and mental disorders caused by the functional impairment of such neurons.

Test Example 6

Effect on Performance in a Radial-Arm Maze Task:

In accordance with the method described by Thomas, J. W. et al. in Brain Research, 321, 91-102, 1984, 0.05 nmol of AF64A picryl sulfonate (hereunder abbreviated as AF64AP) was injected into the both sides lateral cerebral ventricles of male rats (F344) that had been made to acquire the ability to solve a radial-arm maze problem in accordance with the method of Olton and Samuelson (Olton, D. S. and Samuelson. R.

J., J. Exp. Psychol., 2, 97–116, 1976), so as to impart a damage specific to the hippocampal cholinergic system. The mnemonic ability of the rats was evaluated with the number of correct responses (i.e.. the number of different arms selected in the first 8 choices) being used as a measure of their performance. The rats treated with AF64AP were found to have suffered significant memory impairment compared to the control group.

The treated animals were administered orally a vehicle on day 1, 3 and 5, Compound No. 7 on day 2, 4 and 6 (the dose was 3, 10 and 30 mg/kg on day 2, 4 and 6, respectively), and thereafter checked for their ability to solve a radial-arm maze problem. On each day when the performance subsequent to the administration of Compound No. 7 was compared with the control data (obtained by vehicle administration on the previous day) by a paired t-test, a statistically significant increase in the number of correct responses was observed at 10 mg/kg ($p<0.05$; $n=6$) and 30 mg/kg ($p<0.05$; $n=6$). The results are shown in FIG. 1, with the control data for the first and last days of the test being designated by V. Chance level of correct responses defined by Spetch, M. L. and Wilkie, D. M., Behavior Research Methods and Instrumentations. 12, 377–378, 1980, was expressed by dashed line. All the control data obtained in the test were stable since there was no significant difference among the control data.

The results described above and depicted in FIG. 1 show that the compounds of the present invention will prove effective in improving the cognitive ability of patients suffering from Alzheimer's disease and other types of dementia which are characterized by extensive damage to the central cholinergic system.

What is claimed is:

1. A 4-aminoquinoline or 4-amino-5,6,7,8-tetrahydroquinoline compound represented by the formula:

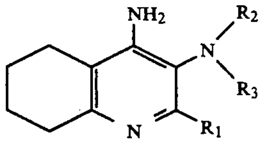

wherein $R_1$ is a hydrogen atom, a hydroxyl group, a linear or branched chain lower alkyl group or a cycloalkyl group which may be substituted by a hydroxyl group, a lower alkoxy group, a lower alkyl group or a cycloalkyl group which contains a carbonyl group, or a group —NH—B where B is a lower alkyl group, a cycloalkyl group, or a phenyl group; $R_2$ and $R_3$, which may be the same or different, each represents a hydrogen atom, a lower alkyl group, a lower alkyl carbonyl group, or when taken together, form a pyrrolidino group, a piperidino group, a morpholino group, or an N-methylpiperazinyl group, together with the nitrogen atom; or an acid addition salt of said quinoline or 5,6,7,8-tetrahydroquinoline compound; and when $R_1$ is a hydrogen atom, $R_2$ and $R_3$ are neither a hydrogen atom nor an ethyl group at the same time.

2. A compound according to claim 1 wherein the lower alkyl group has 1–6 carbon atoms, the lower alkoxy group has 1–6 carbon atoms, and the cycloalkyl group has 3–7 carbon atoms.

3. A compound according to claim 2 wherein the lower alkyl group is a methyl, ethyl, n-propyl, n-butyl or 2-pentyl group, the lower alkoxy group is a methoxy or ethoxy group, and the cycloalkyl group is a cyclohexyl group.

4. A compound according to claim 1, wherein the loweralkylcarbonyl group has 2–7 carbon atoms.

5. A compound according to claim 4 wherein the lower-alkylcarbonyl group is an acetyl or propionyl group.

6. A compound according to claim 1 which is N-[4-amino-2-(cyclohexan-2-on)yl-quinolin]yl-morpholine.

7. A pharmaceutical composition for improving psychoneural function which contains a pharmaceutically acceptable vehicle and an active ingredient which is a 4-aminoquinoline or 4-amino-5,6,7,8-tetrahydroquinoline compound represented by the formula:

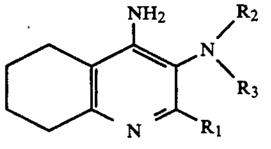

wherein $R_1$ is a hydrogen atom, a hydroxyl group, a linear or branched chain lower alkyl group or a cycloalkyl group which may be substituted by a hydroxyl group, a lower alkoxy group, a lower alkyl group or a cycloalkyl group which contains a carbonyl group, or a group —NH—B where B is a lower alkyl group, a cycloalkyl group, or a phenyl group; $R_2$ and $R_3$, which may be the same or different, each represents a hydrogen atom, a lower alkyl group, a lower alkyl carbonyl group, or when taken together, form a pyrrolidino group, a piperidino group, a morpholino group, or an N-methylpiperazinyl group, together with the nitrogen atom; or an acid addition salt of said quinoline or 5,6,7,8-tetrahydroquinoline compound; and when $R_1$ is a hydrogen atom, $R_2$ and $R_3$ are neither a hydrogen atom nor an ethyl group at the same time.

8. A pharmaceutical composition according to claim 7, which is effective in the treatment of Alzheimer type dementia.

9. A pharmaceutical composition according to claim 7 which is effective in the treatment of pathergasia due to impaired monoaminergic neurons.

10. A pharmaceutical composition according to claim 7, which is effective in promoting mnemonic and learning performance.

11. A pharmaceutical composition according to claim 7 wherein the active ingredient is N-[4-amino-2-(cyclohexan-2-on)yl-quinolin]yl-morpholine.

* * * * *